US009380777B2

(12) United States Patent
Mason et al.

(10) Patent No.: US 9,380,777 B2
(45) Date of Patent: Jul. 5, 2016

(54) FORMULATION COMPRISING A PARTICULATE CALCIUM SILICATE AND CLONOSTACHYS ROSEA FOR TREATING PLANTS

(71) Applicant: BEE VECTORING TECHNOLOGY INC., Caledon (CA)

(72) Inventors: Todd Gordon Mason, Oakville (CA); John Clifford Sutton, Ariss (CA)

(73) Assignee: Bee Vectoring Technology Inc., Mississauga, Ontario (CA)

(*) Notice: Subject to any disclaimer, the term of this patent is extended or adjusted under 35 U.S.C. 154(b) by 0 days.

(21) Appl. No.: 14/483,345

(22) Filed: Sep. 11, 2014

(65) Prior Publication Data

US 2015/0023906 A1 Jan. 22, 2015

Related U.S. Application Data

(63) Continuation of application No. PCT/CA2013/050179, filed on Mar. 11, 2013.

(60) Provisional application No. 61/609,540, filed on Mar. 12, 2012.

(51) Int. Cl.

| | |
|---|---|
| ***A01N 59/06*** | (2006.01) |
| ***A01N 63/00*** | (2006.01) |
| ***A01N 25/22*** | (2006.01) |
| ***A01N 25/08*** | (2006.01) |
| ***A01N 65/00*** | (2009.01) |

(52) U.S. Cl.

CPC ................ *A01N 25/22* (2013.01); *A01N 25/08* (2013.01); *A01N 65/00* (2013.01)

(58) Field of Classification Search

None

See application file for complete search history.

(56) References Cited

U.S. PATENT DOCUMENTS

| | | | |
|---|---|---|---|
| 3,034,949 | A | 2/1962 | Ryker |
| 3,833,731 | A | 9/1974 | Grier et al. |
| 5,348,511 | A | 9/1994 | Gross et al. |
| 5,989,100 | A | 11/1999 | Kovach |
| 6,306,386 | B1 | 10/2001 | Cole et al. |
| RE38,958 | E | 1/2006 | Stimac et al. |
| 2011/0280839 | A1 | 11/2011 | Ford |
| 2015/0050244 | A1 | 2/2015 | Ford |

FOREIGN PATENT DOCUMENTS

| | | | |
|---|---|---|---|
| CN | 102341493 | A | 2/2012 |
| DE | 10054048 | A1 | 5/2002 |
| GB | 1470385 | A | 4/1977 |
| WO | 0294014 | A1 | 5/2002 |
| WO | 2007/030557 | A2 | 3/2007 |
| WO | WO 2007096833 | * | 8/2007 |
| WO | 2010136599 | A2 | 2/2010 |
| WO | 2010108267 | A1 | 9/2010 |
| WO | WO 2010108267 | * | 9/2010 |
| WO | 2011026983 | A1 | 3/2011 |
| WO | 2011097749 | | 8/2011 |

OTHER PUBLICATIONS

Mommaerts et al., Entomovectoring in plant protection, Arthropod-Plant Interactions, 2011, 5:81-95.*

Kapongo et al., Covectoring of Beauveria bassiana and Clonostachys rosea by bumble bees for control of insect pests and suppression of grey mould in greenhouse tomato and sweet pepper, Biological Control, 46, 2008, 508-14.*

Datnoff et al. Chapter 10 The Use of Silicon for integrated disease management: reducing fungicide applications and ennhancing host plant resistance. pp. 171-184. 2011.

Dedej, et al. Effectiveness of Honey Bees in delivering the biocontrol agent Bacillus subtilis to blueberry flowers to suppress mummy berry disease. Available online at www.sciencedirect.com, Aug. 27, 2004. pp. 422-427.

Jyoti et al, Honey Bees (Hymenoptera, Apidae) as Vectors of Bacillus thuringiensis for Control of Banded Sunflower Moth (Lepidoptera: Tortricidae). Department of Entomology, North Dakota State University, Fargo, ND 58105. Dec. 1999 vol. 28 No. 6. pp. 1172-1176.

Les Shipp. BPI10-010 Design of a commercial dispenser for delivery of biocontrol agents in greenhouse by bee pollinators. Agriculture Canada. Issued May 18, 2011.

Kevan. Pollinating bees can now supress crop pests. The Grower. vol. 62 No. 01. Jan. 2012. p. 14.

Yu et al. Effectiveness of Bumblebees and Honeybees for Deliveering Inoculum of Gliocladium roseum to Raspberry Flowers to Control Botrytis cinerea. Biological Control Article No. BC970562. Department of Environmental Biology, University of Guelph. Jul. 7, 1997.

Mommaerts et al. Entomovectoring in plant protection. Arthropod-Plant Interaction 2011. pp. 81-95. Published online Jan. 26, 2011.

Kevan et al. Bee Pollination in Agricultural Ecosystems. Honey Bees, Bumble Bees, and Biocontrol. New Alliances Between Old Friends. Bee-Provided Delivery Services. Oxford University Press 2008. pp. 65-79.

Harrison. Blog. Latest Buzz from Harrow. http://www.greenhousecanada.com/inputs/biocontrols/latest-buzz-from . . . (May 13, 2011)accessed on Jun. 3, 2015.

Kapongo et al. Co-Vectoring of Beauveria bassiana and Clonostachys rosea by bumble bees (bombus impatiens) for control of insect pests and suppression of grey mould in greenhouse tomato and sweet pepper. Biological Control 46 (2008) 508-514. Journal homepage: www.elsevier.com/locate/ybcon.

Peng et al. Summary. Effectiveness of Honeybees for Applying the Biocontrol Agent Gliocladium Roseum to strawberry flowers to suppress Botrytis cinerea. Canadian Journal of Plant Pathology. vol. 14 No. 02. pp. 117-129. Jun. 1992.

Peng et al. Article. Effectiveness of Honeybees for Applying the Biocontrol Agent Gliocladium Roseum to strawberry flowers to suppress Botrytis cinerea. Canadian Journal of Plant Pathology. vol. 14 No. 02. pp. 117-129. Jun. 1992.

* cited by examiner

*Primary Examiner* — Alton Pryor

(74) *Attorney, Agent, or Firm* — Bereskin & Parr LLP/S.E.N.C.R.L., s.r.l.

(57) ABSTRACT

A powder plant treatment formulation for application to plants by insect vectoring includes: a plant treatment agent; a stabilizing agent bonded to the plant treatment agent for stabilizing the plant treatment agent; a moisture absorption agent for absorbing moisture from the formulation; an attracting agent for attracting the formulation to plants; and a diluent.

14 Claims, No Drawings

FORMULATION COMPRISING A PARTICULATE CALCIUM SILICATE AND CLONOSTACHYS ROSEA FOR TREATING PLANTS

CROSS-REFERENCE TO RELATED APPLICATIONS

This application is a continuation of PCT Patent Application No. PCT/CA2013/050179, filed Mar. 11, 2013, which claims priority from U.S. Provisional Patent Application No. 61/609,540, filed Mar. 12, 2012. The entire contents of PCT Patent Application No. PCT/CA2013/050179 and U.S. Provisional Patent Application No. 61/609,540 are hereby incorporated by reference.

FIELD

The disclosure relates to a plant treatment formulation. Specifically, the disclosure relates to a plant treatment formulation which may be disseminated to plants by insect vectoring, such as bee vectoring.

BACKGROUND

U.S. Pat. No. 5,348,511 (Gross et al.) purports to disclose biocontrol agents that are disseminated for the control of pests by *Apis mellifera* L. using a device inserted into a modified down-sized super which is integrated as a substructure of a conventional, commercial beehive. The device provides separate entry and departure pathways which allows exiting bees to be surface-contaminated with the biocontrol agent as they exit the hive.

U.S. Pat. No. 5,189,100 (Kovach) purports to disclose a bee dissemination device or dispenser that is non destructive to the hive, is easy to insert, refill, and remove, and includes a cartridge insertable in a housing. The device is designed to be used by a non professional bee keeper, such as a grower. It is inserted into the entrance of a standard bee hive with minimal disruption to the hive or colony. When the bees exit the hive, they walk up a ramp through a dry biological control suspension and leave the hive, carrying and depositing the biological control agent onto the flowers as they pollinate the crop. When the biological control agent runs low, additional material is added easily by lifting a hinged lid or replacing the old cartridge with a filled one. The lid also provides some moisture protection to keep the biological agent dry, thereby facilitating bee inoculation. The dispenser is removed by simply pulling it from the hive entrance when pollination activities are completed. The removal is non disruptive and does not destroy the integrity of the hive. When the device is inserted, refilled, or removed at night, minimal protective clothing is required by the user.

PCT patent application publication no. WO 2010/136599 (Put et al.) purports to disclose the dissemination of biological control agents or other substances through the use of bees, in particular bumblebees. A disseminator device is installable in or in connection to the hive, and contains biological control agents or other substances which are picked up, carried and disseminated by the bees when leaving the hive.

SUMMARY

The following summary is intended to introduce the reader to various aspects of the applicant's teaching, but not to define any invention.

According to one aspect, a formulation for treatment of plants comprises a particulate calcium silicate, and a plant treatment agent combined with the particulate calcium silicate.

According to another aspect, a biocontrol powder formulation for application to plants by insect vectoring comprises: a plant treatment agent; a stabilizing agent bonded to the plant treatment agent for stabilizing the plant treatment agent; a moisture absorption agent for absorbing moisture from the formulation; an attracting agent for attracting the formulation to plants; and a diluent.

According to another aspect, a powder formulation for treatment of plants comprises a plant treatment agent comprising spores of *clonostachys rosea*. The formulation comprises between about $2\times10^8$ and about $4\times10^8$ spores per gram of formulation.

According to another aspect, a method for preparing a plant treatment formulation comprises: providing a suspension of a plant treatment agent in a liquid; providing particulate calcium silicate; and bonding the suspension to the calcium silicate;

According to another aspect, a method for preparing a plant treatment formulation comprises: bonding spores of *clonostachys rosea* to a particulate stabilizing agent to produce stabilized plant treatment particles; combining the stabilized plant treatment particles with at least one additive to produce a mixture of the stabilized plant treatment particles and the additive; and adding free stabilizing agent to the mixture to adjust the concentration of the spores in the formulation to between about $2\times10^8$ and about $4\times10^8$ spores per gram of formulation.

According to another aspect, a formulation for the treatment of plants by insect vectoring comprises a plant treatment agent, and a particulate moisture absorption agent for absorbing moisture from the formulation. The moisture absorption agent has a particle size selected to be too large to be vectored by insects. In some examples, the moisture absorption particle size may be greater than the size of the stabilized plant treatment particles. In some examples, the moisture absorption particles may have a size from about 15 to about 90 times greater than the size of the stabilized plant treatment particles.

According to another aspect, *clonostachys rosea* is used to treat *botrytis cinerea* in canola.

According to another aspect, *clonostachys rosea* is used to treat *sclerotinia sclerotiorum* in canola.

In some examples, the plant treatment agent may be bonded to at least some of the calcium silicate to form stabilized plant treatment particles. The formulation may comprise between about 5 wt % and 15 wt % stabilized plant treatment particles, more specifically between about 7 wt % and 8 wt % stabilized plant treatment particles.

In some examples, at least some of the calcium silicate may be free calcium silicate. The formulation may comprise between about 10 wt % and 25 wt % free calcium silicate, more specifically between about 17 wt % and 18 wt % free calcium silicate.

In some examples, the plant treatment agent may comprise a microbial agent. For example, the plant treatment agent may comprise a fungal spore such as *clonostachys rosea*. For further example, the plant treatment agent may comprise *beauveria bassiana*.

In some examples, the plant treatment agent may comprise a fungal spore, and the fungal spore may be bonded to at least some of the calcium silicate. The plant treatment agent may have a density of between about $1\times10^9$ and $4\times10^9$ spores per gram of calcium silicate to which it is bonded, more specifically about $2\times10^9$ spores per gram of calcium silicate to which it is bonded.

In some examples, formulation may comprise between about $2\times10^8$ and about $4\times10^8$ spores per gram of formulation.

In some examples, the particulate calcium silicate may comprise particles having a sieve designation of between about 45 microns and about 75 microns, more specifically about 45 microns.

In some examples, a moisture absorption agent may be mixed with the particulate calcium silicate and plant treatment agent. The moisture absorption agent may comprise silica gel. The silica gel may comprise particles having a sieve designation of between about 700 microns and 4000 microns, more specifically about 840 microns. The formulation may comprise between about 0.5 wt % and 5 wt % moisture absorption agent, more specifically about 1 wt % moisture absorption agent.

In some examples, the formulation may further comprise an attracting agent mixed with the particulate calcium silicate and plant treatment agent, for attracting the formulation to plants and/or vectoring insects. The attracting agent may have a net positive electrostatic charge. The attracting agent may comprise a mixture of minerals. The formulation may comprise between about 5 wt % and about 20 wt % attracting agent, more specifically about 10 wt % attracting agent. The attracting agent may have a sieve designation of between about 35 microns and about 75 microns, more specifically about 45 microns.

In some examples, the formulation may further comprise a diluent mixed with the particulate calcium silicate and plant treatment agent. The diluent may comprise a flour, such as at least one of rye flour, wheat flour, spelt flour, rice flour, and corn flour. In one particular example the diluent comprises corn flour. The formulation may comprise between about 50 wt % and 75 wt % diluent, more specifically about 64 wt % diluent. The diluent may have a sieve designation of between about 75 microns and about 250 microns, more specifically about 125 microns.

In some examples, the formulation may further comprise an anti-caking agent. The anti-caking agent may comprise magnesium oxide. The formulation may comprise between about 0.75 wt % to 5.0 wt % magnesium oxide, more specifically between about 1 wt % and about 1.5 wt % magnesium oxide. The anti-caking agent may have a sieve designation of between about 75 microns and about 150 microns, more specifically about 125 microns.

In some examples, the formulation may be used to treat at least one of *sclerotinia sclerotiorum, botrytis cinerea*, and *Monilinia vaccinii-corymbosi* in a plant.

In some examples, the formulation may be used to treat a disease in at least one of canola plants and sunflower plants.

In some examples, the formulation may be used to increase the germination rate in a crop.

In some examples, the formulation may be used as a bee vectoring agent.

DETAILED DESCRIPTION

Various apparatuses, processes, and/or formulations will be described below to provide an example of an embodiment of each claimed invention. No embodiment described below limits any claimed invention and any claimed invention may cover apparatuses, processes, and/or formulations that differ from those described below. The claimed inventions are not limited to apparatuses, processes, and/or formulations having all of the features of any one apparatus, process, and/or formulation described below, or to features common to multiple or all of the apparatuses, processes, and/or formulations described below. It is possible that an apparatus, process, and/or formulation described below is not an embodiment of any exclusive right granted by issuance of this patent application. Any invention disclosed in an apparatus, process, and/or formulation described below and for which an exclusive right is not granted by issuance of this patent application may be the subject matter of another protective instrument, for example, a continuing patent application, and the applicants, inventors or owners do not intend to abandon, disclaim or dedicate to the public any such invention by its disclosure in this document.

Exemplary plant treatment formulations include a plant treatment agent (i.e. an agent that is beneficial to a crop), and one or more additives. For example, a plant treatment agent may promote the growth, vigor, and productivity of plants; enhance germination rates and/or seed quality in a crop; enhance resistance to disease, pests, and/or environmental stresses such as adverse weather or soil conditions; control or act against disease or pests; or promote the recovery of plants from injury and/or infection.

In some examples, the plant treatment agent may include one or more microbes, such as a bacteria, a virus, or a fungus or fungal spore. One example of a suitable fungal spore includes *clonostachys rosea*, which may control pathogens such as *sclerotinia sclerotiorum, monilinia vaccinii-corymbosi*, and/or *botrytis cinerea* in various crops, including canola, sunflower, raspberry, blueberry, strawberry, apple, pear, kiwi, watermelon, coffee, mango, avocado, cherry, plum, almond, peach, cashew, guava, alfalfa, buckwheat, clover, bean, pea, onion, soybean, cotton, mustard, blackberry, gooseberry, pepper, eggplant, and currant. Another example of a suitable fungal spore includes *beauveria bassiana*, which may control cranberry maggot in cranberry crops. One example of a suitable bacteria is *Bacillus Thuringiensis*, which may control insect pests in various crops.

The concentration of the plant treatment agent in the formulation may vary depending on, for example, the nature of the plant treatment agent, and/or the conditions in which the formulation is to be used (e.g. climate, target plant, etc.). In one particular example, wherein the plant treatment agent includes spores of *clonostachys rosea*, the formulation may include between about $2\times10^8$ and $4\times10^8$ spores per gram of formulation.

The formulation may include various additives combined with the plant treatment agent. In some examples, the additives include one or more of a stabilizing agent, a moisture absorption agent, an attracting agent, a diluent, and/or an anti-caking agent, as will be described in further detail below.

Stabilizing agents may generally serve to prevent or minimize decay, breakdown, or activation of the plant treatment agent prior to delivery of the plant treatment agent to the plant target. For example, in cases wherein the plant treatment agent is a fungal spore, the stabilizing agent may absorb water to keep the fungal spore relatively dry, and thereby stabilize the spores in a dormant state and prevent or minimize germination of the spores prior to the delivery of the spores to a plant.

One example of a stabilizing agent is particulate calcium silicate (sold under the trade name Micro-Cel®). The particles of calcium silicate may have a sieve designation of between about 45 microns (about 325 mesh) and about 75 microns (about 200 mesh). In one particular example, the particles of calcium silicate have a sieve designation of about 45 microns (325 mesh).

In some examples, the plant treatment agent may be bonded to at least some of the stabilizing agent, to produce stabilized plant treatment particles. For example, a suspension of fungal spores in water may be sprayed onto calcium silicate particles, so that the fungal spores generally adhere to the calcium silicate particles. The suspension of fungal spores may be prepared as described in United States Patent Application Publication no. US 2012/0021906 (Sutton et al.), incorporated herein by reference in its entirety. The stabilized plant treatment particles may have a spore density of between about $1\times10^9$ and about $4\times10^9$ spores per gram of calcium silicate to which the spores are bonded. In one particular example, the stabilized plant treatment particles have a spore density of about $2\times10^9$ spores per gram of calcium silicate to which the spores are bonded.

In some examples, the formulation may include between about 5 wt % and about 15 wt % stabilized plant treatment particles, more specifically between about 7 wt % and about 8 wt % stabilized plant treatment particles. In one particular example, the formulation may include 7.5 wt % stabilized plant treatment particles.

In some examples, at least some of the stabilizing agent may be mixed into the formulation without being bonded to the plant treatment agent. Such stabilizing agent may be referred to as free stabilizing agent. The amount of free stabilizing agent in the formulation may optionally be selected to yield a formulation having a particular concentration of plant treatment agent. For example, the components of the formulation may be mixed together, and then free stabilizing agent may be added to the formulation until the concentration of spores in the formulation reaches a concentration of between about $2\times10^8$ and $4\times10^8$ spores per gram of formulation. In such examples, the formulation may include between about 10 wt % and about 25 wt % free stabilizing agent, more specifically between about 17 wt % and about 18 wt % free stabilizing agent. In one particular example, the formulation may include about 17.5 wt % free stabilizing agent.

The moisture absorption agent may absorb moisture from the formulation, in order to keep the formulation relatively dry and prevent caking or clumping of the formulation. Examples of moisture absorption agents include dessicants, such as particles or beads of silica gel, and super absorbent polymers, such as sodium polyacrylate. Further examples of moisture absorption agents include wood shavings, and clay balls. In some examples, the formulation may include between about 0.5 wt % and 5 wt % moisture absorption agent. In one particular example, the formulation may include about 1 wt % moisture absorption agent.

In examples wherein the formulation is to be delivered by insect vectoring, the particle size of the moisture absorption agent may be selected so that it is too large to be carried by insects, and will therefore generally remain in the disseminator, in order to continue to absorb moisture from the formulation. For example, the particles may have a sieve designation of between about 700 microns (25 mesh) and about 4000 microns (5 mesh). In one particular example, the silica gel may be in the form of particles having a sieve designation of about 840 microns (20 mesh).

The attracting agent may help to attract the formulation to plants and/or vectoring insects. For example, the attracting agent may have a net positive electrostatic charge, so that it is electrostatically attracted to plants and/or vectoring insects, which have a net negative electrostatic charge. In some examples, the attracting agent may include a mineral, or a mixture of minerals. In one particular example, the attracting agent may include a mineral mixture sold by Agri-Dynamics (Martins Creek, Pa.) under the name DYNA-MINT™, which includes the following minerals: silicon dioxide, aluminum oxide, calcium, iron, magnesium, potassium, sodium, phosphorus, titanium, manganese, strontium, zirconium, lithium, rubidium, boron, zinc, vanadium, chromium, copper, yttrium, nickel, cobalt, gallium, cesium, scandium, tin, molybdenum, and additional trace elements. In another example, the attracting agent may include calcium limestone.

In some examples, the formulation may include between about 5 wt % and about 20 wt % attracting agent. In one particular example, the formulation may include about 10 wt % attracting agent. In some examples, the attracting agent may have a sieve designation of between about 35 microns (about 350 mesh) and about 75 microns (about 200 mesh). In one particular example, the attracting agent may have a sieve designation of about 45 microns (about 325 mesh).

The diluent may be a suitable starch or flour. In examples wherein the formulation is to be delivered by insect vectoring, the diluent may be selected so that it does not irritate or harm the insects, and will not be eaten by the insects. The diluent may further be selected so that it does not absorb significant amounts of moisture, so that the diluent does not clump. Examples of diluents which may be suitable for insect vectoring include corn flour, and grain flours such as rye, wheat, rice flour, and spelt flour. In alternate examples, the diluent may be kaolin. In other examples the diluent may comprise milk powder or talc. These may be particularly useful in examples wherein the formulation is delivered in a manner other than insect vectoring, such as by spraying.

In some examples, the formulation may include between about 50 wt % and about 75 wt % diluent. In one particular example, the formulation may comprise about 64 wt % diluent. In some examples, the diluent may have a sieve designation of between about 75 microns (about 200 mesh) and about 250 microns (about 60 mesh). In one particular example, the diluent may have a sieve designation of about 125 microns (about 125 mesh).

The formulation may include any suitable anti-caking agent. One particular example of an anti-caking agent is magnesium oxide. The formulation may include between about 0.75 wt % and about 5.0 wt % anti-caking agent, and more specifically, between about 1 wt % and about 1.5 wt % anti-caking agent. In one particular example, the formulation may include 1.25 wt % anti-caking agent. In some examples, the anti-caking agent may have a sieve designation of between about 75 microns (about 200 mesh) and about 150 microns (about 100 mesh). In one particular example, the anti-caking agent has a sieve designation of about 125 microns (about 125 mesh).

The plant treatment formulation may be prepared by a variety of methods. In one example, the stabilized plant treatment particles are prepared as described above, by bonding a plant treatment agent such as a fungal spore to a stabilizing agent. The stabilized plant treatment particles may then be combined with the additives, such as one or more of the moisture absorption agent, the attracting agent, the diluent, and the anti-caking agent. For example, the additive(s) may be mixed with the stabilized plant treatment particles. Optionally, additional free stabilizing agent may then be added to the mixture, to adjust the concentration of spores to a desired value. For example, free stabilizing agent may be added to adjust the concentration of spores to between about $2\times10^8$ and about $4\times10^8$ spores per gram of formulation.

In some examples, after the formulation is placed in a disseminator or otherwise made available to insects for insect vectoring, the shelf life of the formulation may be 4 to 5 days. In alternate examples, the shelf life may be longer, for example up to 10 days. The shelf life of the formulation may vary depending on various factors, including ambient humidity, and temperature, for example.

The formulation described above may be particularly useful in insect vectoring. However, the formulation may be disseminated in other ways, such as by spraying.

While the above description provides examples of one or more processes, formulations, or apparatuses, it will be appreciated that other processes, formulations, or apparatuses may be within the scope of the accompanying claims.

EXAMPLES

Example 1

Preparation of Plant Treatment Formulation

A plant treatment formulation of the following composition was prepared:

| | |
|---|---|
| 7.5 wt % | Stabilized plant treatment particles of clonostachys rosea bonded to Microcel ® (325 mesh, 44 micron) at a density of $2 \times 10^9$ spores per gram of microcell; |
| 17.5 wt % | Free Microcel ® (325 mesh, 44 micron); |
| 1.25 wt % | Magnesium oxide (125 mesh, 125 micron); |
| 10 wt % | Dyna-min ™ (325 mesh, 44 micron); |
| 64 wt % | Corn flour (125 mesh, 125 micron); |
| 1 wt % | Silica gel (about 20 mesh, 700 to 1000 micron); |

The formulation was prepared by spraying a suspension of *clonostachys rosea* onto Microcel® particles. The resulting particles were mixed with the magnesium oxide, Dyna-Min™, corn flour, and silica gel. The free Microcel® was then added to adjust the concentration of spores to approximately $3\times10^8$ spores per gram of formulation.

Example 2

Acquisition of Plant Treatment AGent by Bumble Bees when Exiting Hives Via Dispensers Bumble bee hives, each with a colony of bumble bees (Bombus impatiens), were equipped with a dispenser through which the bees were directed to travel when exiting the hive.

The hives were positioned on a bench in a research greenhouse. The bees were confined inside large mesh cages. The new colonies were left alone to acclimate and become accustomed to their new surroundings for 24 hours. After the 24 hour period, the dispenser was filled with the formulation described in Example 1, so that the bees would be directed to walk through a bed of the formulation when exiting the hive.

Individual bumble bees were captured as they exited the hive. Each bee was placed inside a 1.5 mL microcentrifuge ("microfuge") tube and the attached cap was closed. The tubes with the captured bees were stored in a refrigerator for a few hours (2-12 hours) and then processed to estimate the numbers of spores adhering to each bee.

Each bee was washed in a known volume of water (including a wash from the inside wall of the microfuge tube) containing a surfactant (0.01% Triton X-100 v/v), and vigorously agitated five times (about 5 sec each time) on a Vortex (Fisher Genie 2). The water and bee was allowed to stand for 10 minutes before the "wash water" was serially diluted.

Aliquots of 0.5 ml of the "wash water" were serially diluted (10-fold dilutions) and 0.1 mL of each dilution was spread onto PDTSA (potato dextrose agar medium amended with Triton X-100 (0.01% or roughly 8 drops/L) to reduce the rate of colony growth (and to separate the colonies for counting) and streptomycin sulfate at 100 ppm to keep down bacteria) in Petri dishes. For each bee, 3 serial dilutions were performed and three 0.1 mL aliquots of each dilution were plated onto the PDTSA. The Petri dishes were incubated for 4-5 days at about 22-24 C. (70-74 F. or room temperature) by which time colonies of *Clonostachys rosea* had developed and the colonies were counted. The colony counts were multiplied by the relevant dilution factor, multiplied by 10 (because only 0.1 mL was plated), and adjusted for the total volume of water used for washing the bee. This gave the estimated number of viable (colony forming) units of *Clonostachys rosea* per bee. As shown in table 1, the bees in these tests generally carried about 100,000 to 125,000 viable spores of *Clonostachys rosea* each time they exited the dispenser on their way out of the hive.

TABLE 1

| | Number of Colony Forming Units/Bee (average of three serial dilutions per bee) | | | |
|---|---|---|---|---|
| Test # | Bee #1 | Bee #2 | Bee #3 | Bee #4 |
| 1 | $1.14 \times 10^5$ | $1.02 \times 10^5$ | $1.21 \times 10^5$ | $0.99 \times 10^5$ |
| 2 | $1.25 \times 10^5$ | $1.18 \times 10^5$ | $1.11 \times 10^5$ | — |
| 3 | $0.97 \times 10^5$ | $1.09 \times 10^5$ | $1.09 \times 10^5$ | $1.23 \times 10^5$ |

Microscopic examination of bees revealed that particles of the powder were present especially on the legs and undersides of the bees (all of these are hairy).

Example 3

Assessment of Sunflowers Treated with Bumble Bee-Vectored *Clonostachys rosea* and *Bacillus Thuringiensis*

Field 1:

A first test site included a 20 acre sunflower field (field 1), that was 200 m wide, and that ran from country road along the east side of the field. Five groups of four bumble bee domiciles (quads) were set up in the field in July of 2011. The domiciles were positioned at regular intervals next to the roadway at the edge of the area with sunflowers, and were thus readily accessible. Each domicile was equipped to receive a tray containing a powdered plant treatment formulation in an exit pathway of the domicile. Trays containing a plant treatment formulation were inserted into the domiciles. The formulation was prepared as described in example 1, but further included *Bacillus Thuringiensis* ($2\times10^8$ spores per gram of formulation). The trays were inserted into the domiciles in July of 2011, and replaced about every 3 days until August 2011.

It was observed that the flowering period of the early planted sunflowers in the field was shortened by hot weather (daily highs of 35-38° C.) in the second half of July.

The trays were examined on Aug. 10, 2011. The powdered plant treatment formulation was observed to be dry and was not clumping.

Samples of sunflowers were taken on Aug. 10, 2011. It was observed that about 75-80% of the flowers had lost the large peripheral petals. Some rain had occurred during the preceding 1-3 days (surface soil was moist).

SAMPLING: Sunflower heads were sampled in relation to quad #2 (i.e. the second from the road) and quad #4 (i.e. the fourth from the road). The heads were collected at five distances (at 3 m, 40 m, 80 m, 120 m, and 160 m) from the quad in a transect made across the field at right angles to the road. Four heads were taken at each sampling distance, placed in plastic patch bags and transported to a laboratory.

PROCESSING OF THE SAMPLES: The incidence of *Clonostachys rosea* in florets from the sunflower heads collected was estimated by placing florets on Paraquat chloramphenicol agar (PCA), and later examining for sporulation of the fungus, in accordance with the following procedure:

A total of about 160-200 florets were plucked using repeatedly sterilized forceps from about 12-15 random areas of each sunflower head. Each area was in the zone with developing seeds (i.e. not from the centre of the heads) and about 1.0-1.5 cm across. About half of the florets from each head were scattered (separately as far as practical) onto PCA in each of two Petri dishes. The Petri dishes with the florets were placed in translucent plastic boxes and incubated away from direct sunlight. The florets were somewhat fluffy and did not make good contact with the agar medium, but nonetheless senesced and turned pale brown uniformly ("in concert").

The sunflower heads from which florets were removed were placed in a cold room.

The plated florets were checked visually for sporulation of *Clonostachys rosea* after 5 and 7 days of incubation and assessed microscopically after 8 days and again after another 18 days. At each time of assessment, the florets in each dish were rated collectively for sporulation incidence of *Clonostachys rosea* using the following equal-increment scale: 0=no sporulation; 1=1-10% of florets with sporulation; 2=11-20%; 3=21-30% . . . 10=91-100%. In tables 2 and 3 below these values are presented in columns for Petri dishes A and B for each of four sunflower heads. The midpoints of the ranges (i.e. 0%, 5%, 15%, 25% . . . 95%) on the scale were used to give estimated % values. Mean % values per head were derived from midpoint values for the ratings in columns A and B. The mean % values for the four heads collected at given distances from the domiciles provided an overall estimated mean % of florets on which *Clonostachys rosea* sporulated (values in bold in the column at the right of each table).

RESULTS AND DISCUSSION—8 DAYS AFTER PLATING: Tables 2 and 3 below show results for assessments at 8 days after plating. These tables show an estimation for the mean percent of florets with *Clonostachys rosea*, which is a measure of the success in vectoring the plant treatment agent to the flowers.

*Clonostachys rosea* was found sporulating on various (or all) parts of florets.

Little growth (i.e. mycelium and/or sporulation) of other fungi was found on florets with sporulation of *Clonostachys rosea*. This is in contrast to florets with no *Clonostachys rosea*. This was clear for florets in a Petri dish in which the agar was presumably contaminated with spores of *Clonostachys rosea* prior to use. In this circumstance, *Clonostachys rosea* sporulated heavily on all the florets, but almost no other fungal growth was present. The finding that other fungi were sparse or absent from florets with *Clonostachys rosea* sporulation suggests that *Clonostachys rosea* was generally first to establish (presumably endophytically) in the florets and precluded subsequent establishment and growth of other. This also indicated that *Clonostachys rosea* is ecologically very well adapted for colonization of sunflower florets.

Florets on which *Clonostachys rosea* did not sporulate were covered with masses of mycelium and sporulation of other fungi when assessed on day 8 (and earlier). These fungi are species that are very common on various kinds of senescing plant tissues and included: *Alternaria alternata* (abundant); *Cladosporium* spp. (abundant); *Penicillium* spp and *Aspergillus* spp. (both common); *Epicoccum* sp. (low frequency); *Fusarium* spp. (low frequency); and *Rhizopus* (not frequent). These fungi were probably present as spores (or other propagules) on the surfaces of the florets when the sunflowers were taken in the field and when the florets were plated onto PCA. They are not considered to be endophytes. *Rhizopus* can cause neck and head rot of sunflower (one head was found in an adjacent field with neck and head rot that turned out to be caused by *Rhizopus* when plated in the lab)

The *Clonostachys rosea* recovered from the florets is presumed to have been vectored to the sunflower heads by the bumble bees. The incidence of sunflower heads from which *Clonostachys rosea* was recovered was 35% for transect #1 and 55% for transect 2. The incidence of florets (including those from heads with no detected *Clonostachys rosea*) was generally low (about 2-6% for transect 1 and 0-11% for transect 2).

TABLE 2

Transect 1 (for quad #2)

| Distance from Hives (m) | Head number 1 A | B | Mean % | 2 A | B | Mean % | 3 A | B | Mean % | 4 A | B | Mean % | MEAN %** |
|---|---|---|---|---|---|---|---|---|---|---|---|---|---|
| 3 | 0 | 1 | 2.5 | 0 | 0 | 0 | 1 | 0 | 2.5 | 1 | 0 | 2.5 | **1.88** |
| 40 | 0 | 0 | 0 | 2 | 0 | 7.5 | 1 | 1 | 5.0 | 0 | 0 | 0 | **3.13** |
| 80 | 1 | 0 | 2.5 | 0 | 0 | 0 | 0 | 1 | 2.5 | 0 | 2 | 7.5 | **3.13** |
| 120 | 1 | 1 | 5.0 | 1 | 1 | 5.0 | 3 | 0 | 12.5+ | 1 | 0 | 2.5 | **6.25** |
| 160 | 0 | 0 | 0 | 1 | 0 | 2.5 | 0 | 0 | 0 | 0 | 1 | 2.5 | **1.25** |

TABLE 3

Transect 2 (for quad #4).

| Distance from Hives (m) | Head number 1 A | B | Mean % | 2 A | B | Mean % | 3 A | B | Mean % | 4 A | B | Mean % | MEAN % |
|---|---|---|---|---|---|---|---|---|---|---|---|---|---|
| 3 | 1 | 1 | 5.0 | 2 | 2 | 15 | 2 | 1 | 10 | 0 | 0 | 0 | **7.50** |
| 40 | 2 | 1 | 10 | 10* | 2 | 15 | 1 | 2 | 10 | 1 | 2 | 10 | **11.25** |
| 80 | 0 | 2 | 7.5 | 0 | 0 | 0 | 0 | 2 | 7.5 | 1 | 0 | 2.5 | **4.38** |
| 120 | 2 | 1 | 10 | 1 | 1 | 5.0 | 1 | 2 | 10 | 0 | 0 | 0 | **6.25** |
| 160 | 0 | 0 | 0 | 0 | 0 | 0 | 0 | 0 | 0 | 0 | 0 | 0 | **0.00** |

*This plate was clearly contaminated with *C. rosea* when in the lab and discarded. The data were therefore were not included in estimates.

*Clonostachys* was vectored for at least 160 m in transect 1 and 120 m in transect 2.

There was no good evidence that consistent gradients existed in the vectoring transects (such as decline with distance from the bumble bee colony boxes). The incidence data suggest that vectoring was fairly even.

RESULTS AND DISCUSSION—18 DAYS AFTER PLATING: Tables 4 and 5 below show results for assessments at 18 days after plating. These tables show an estimation for the mean percent of florets with *Clonostachys rosea*, which is a measure of the success in vectoring the plant treatment agent to the flowers.

TABLE 4

| Transect 1 (for quad 2) | | | | | | | | | | | | | |
|---|---|---|---|---|---|---|---|---|---|---|---|---|---|
| | Head number | | | | | | | | | | | | |
| | 1 | | | 2 | | | 3 | | | 4 | | | |
| Distance from Hives (m) | A | B | Mean % | A | B | Mean % | A | B | Mean % | A | B | Mean % | MEAN %** |
| 3 | 2 | 2 | 15 | 2 | 4 | 25 | 0 | 0 | 0 | 2 | 1 | 10 | **12.5** |
| 40 | 0 | 0 | 0 | 3 | 4 | 30 | 1 | 3 | 15 | 1 | 2 | 10 | **13.8** |
| 80 | 1 | 0 | 2.5 | 0 | 1 | 2.5 | 5 | 2 | 30 | 1 | 2 | 10 | **11.3** |
| 120 | 0 | 0 | 0 | 2 | 3 | 20 | 3 | 2 | 20 | 5 | 1 | 25 | **16.3** |
| 160 | 0 | 1 | 2.5 | 2 | 2 | 15 | 3 | 4 | 30 | 1 | 4 | 20 | **16.9** |

TABLE 5

| Transect 2 (for quad 4) | | | | | | | | | | | | | |
|---|---|---|---|---|---|---|---|---|---|---|---|---|---|
| | Head number | | | | | | | | | | | | |
| | 1 | | | 2 | | | 3 | | | 4 | | | |
| Distance from Hives (m) | A | B | Mean % | A | B | Mean % | A | B | Mean % | A | B | Mean % | MEAN %** |
| 3 | 5 | 7 | 55 | 7 | 9 | 75 | 5 | 7 | 55 | 3 | 5 | 35 | **55.0** |
| 40 | 3 | 3 | 25 | # | 5 | 45 | 6 | 3 | 40 | 5 | 6 | 50 | **40.0** |
| 80 | 4 | 5 | 40 | 5 | 8 | 60 | 7 | 3 | 45 | 1 | 2 | 10 | **38.8** |
| 120 | 4 | 4 | 35 | 1 | 1 | 2.5 | 1 | 4 | 20 | 2 | 2 | 15 | **18.1** |
| 160 | 2 | 1 | 10 | 3 | 3 | 25 | 1 | 1 | 5 | 2 | 1 | 10 | **12.5** |

Sporulation of *Clonostachys rosea* was much more abundant at 18 days than after 8 days of incubation.

Non-pathogens (*Cladosporium* and *Alternaria*) had grown to cover many of the florets. *Clonostachys rosea* was frequently growing over the mycelium of the non-pathogens and apparently as a parasite (i.e. as a mycoparasite "eating" the other fungi).

*Botrytis cinerea* (gray mold) was found on a few florets (this can be a head-rotting pathogen in wet weather).

Insect frass (relatively large cylindrical pieces) was present and abundant on several plates. Many florets on these plates were partially eaten and appeared very wet. No insect larvae were found.

The greater % incidence of *Clonostachys rosea* on the florets after 18 days of incubation compared to 8 days probably indicates that florets require longer than 8 days on PCA to senesce sufficiently for *Clonostachys rosea* to reach full sporulation incidence. Care was taken to account for some spread of *Clonostachys rosea* among florets during incubation.

Incidence of *Clonostachys rosea* sporulation in the two transects increased several fold over the values for 8 days of incubation. From these data, 8 days of incubation is insufficient to capture the full extent of sporulation (and the implied floret colonization) by *Clonostachys rosea*. For many kinds of plant tissues, such as flat pieces of leaves that make major contact with the Paraquat medium, 8 days is sufficient. But the "hairy" florets tend make only limited contact, at least initially, and so may take longer to senesce.

The mean incidence of sporulation of *Clonostachys rosea* in florets of sunflower heads in transect 2 was about 33% compared to only 14% for transect 1.

At least a few florets with *Clonostachys rosea* were found in all sunflower heads of transect 2, but 10% of heads lacked *Clonostachys rosea* in transect 1.

There was little indication of any gradient in incidence of *Clonostachys rosea* on the florets (and thus the success of vectoring) in transect 1, but a decline in incidence was evident after 80 m in transect 2.

Field 2

A second test site included a sunflower field (field 2) that consisted of 6 acres that were a continuation of field 1, but that were planted later than field 1 on account of wet soil conditions. On Aug. 10, 2011, it was observed that flowering was just beginning. A bumble bee quad was moved from field 1 to field 2 late in the day on Aug. 10, 2011.

About 6 flowers from field 2 were artificially inoculated with the plant treatment formulation described in example 1 on Aug. 10, 2011.

On Aug. 26, 2011, flowers were collected from a transect in field 2 (same distances from the quad as in field 1). The flowers inoculated with the powder formulation by hand were also collected.

Heads and foliage in Field #2 were surveyed for diseases, molds and insects and samples were taken to the lab for diagnosis.

Florets from the sampled flowers were plated on PCA on Aug. 27, 2011, as described above with regards to field 1. The sub-sampled heads were kept in open patch bags for later examination.

Results and Discussion—9 Days after Plating

Table 6 below shows results for assessments at 9 days after plating. This table shows an estimation for the mean percent of florets with *Clonostachys rosea*.

TABLE 6

| Transect 1 | | | | | | | | | | | | | |
|---|---|---|---|---|---|---|---|---|---|---|---|---|---|
| | Head number | | | | | | | | | | | | |
| | 1 | | | 2 | | | 3 | | | 4 | | | |
| Distance from Hives (m) | A | B | Mean % | A | B | Mean % | A | B | Mean % | A | B | Mean % | MEAN %** |
| 3 | 1 | 0 | 2.5 | 1 | 1 | 5 | 0 | 2 | 7.5 | 1 | 1 | 5 | **5.00** |
| 40 | 0 | 2 | 7.5 | 0 | 2 | 7.5 | 0 | 2 | 7.5 | 1 | 0 | 2.5 | **6.25** |
| 80 | 0 | 0 | 0 | 3 | 3 | 25 | 0 | 0 | 0 | 1 | 1 | 2.5 | **6.87** |
| 120 | 2 | 0 | 7.5 | 1 | 2 | 10 | 1 | 1 | 5 | 3 | 0 | 12.5 | **8.75** |
| 160 | 0 | 0 | 0 | 0 | 1 | 2.5 | 2 | 1 | 10 | 1 | 0 | 2.5 | **3.75** |

(Note: insect (sunflower moth) damage was observed on about 20% of the heads. There was one quad nearest the transect, but bees from other quads possibly participated. The quad was found damaged by an animal on Aug. 26, 2011)

RESULTS AND DISCUSSION—15 DAYS AFTER PLATING: Table 7 below shows results for assessments at 15 days after plating. This table shows an estimation for the mean percent of florets with *Clonostachys rosea*.

TABLE 7

| Transect 1 | | | | | | | | | | | | | |
|---|---|---|---|---|---|---|---|---|---|---|---|---|---|
| | Head number | | | | | | | | | | | | |
| | 1 | | | 2 | | | 3 | | | 4 | | | |
| Distance from Hives (m) | A | B | Mean % | A | B | Mean % | A | B | Mean % | A | B | Mean % | MEAN %** |
| 3 | 2 | 2 | 15.0 | 3 | 2 | 20 | 1 | 3 | 15.0 | 1 | 2 | 10 | **15.0** |
| 40 | 2 | 3 | 20.0 | 0 | 3 | 12.5 | 0 | 3 | 12.5 | 3 | 1 | 15.0 | **15.0** |
| 80 | 0 | 0 | 0 | 3 | 4 | 30 | 0 | 0 | 0 | 1 | 4 | 20.0 | **17.5** |
| 120 | 3 | 1 | 15.0 | 2 | 4 | 30 | 4 | 4 | 35 | 4 | 0 | 17.5 | **24.4** |
| 160 | 0 | 2 | 7.5 | 0 | 3 | 12.5 | 3 | 1 | 15.0 | 3 | 1 | 15.0 | **12.5** |

(Note: Insect (sunflower moth) damage was observed on many heads. There was one quad of bumble bee hives nearest the transect, but bees from other quads possibly participated. The quad was found damaged (by an animal) on Aug. 26, 2011.)

RESULTS AND DISCUSSION—HAND INOCULATED HEADS IN FIELD 2: Table 8 shows the results for sunflower heads inoculated by hand. This table shows an estimation for the mean percent of florets with *Clonostachys rosea*.

TABLE 8

| | A | B | Mean |
|---|---|---|---|
| Head #1 | 9 | 8 | 80% |
| Head #2 | 5 | 8 | 60% |
| Head #3 | 3 | 4 | 30% |
| Head #4 | 3 | 3 | 25% |
| Head #5 | 4 | 6 | 45% |

Field 3

A third test site included a sunflower field consisting of approximately 9 acres. Field 3 was in about mid-bloom. A quad as described with regard to field 1 was placed in a roadway that bisects the field and adjacent to sunflowers in one half of the field. Flowers were collected from a transect in Field 3 according to the same sampling procedures and distances from the quad as in fields 1 and 2.

Heads and foliage in Field #3 were surveyed for diseases, molds and insects and samples were taken to the lab for diagnosis.

Florets from the sampled flowers were plated on PCA on Aug. 29, 2011, as described above.

RESULTS AND DISCUSSION—7 DAYS AFTER PLATING: Table 9 below shows results for assessments at 7 days after plating. This table shows an estimation for the mean percent of florets with *Clonostachys rosea*.

TABLE 9

| | Head number | | | | | | | | | | | | |
|---|---|---|---|---|---|---|---|---|---|---|---|---|---|
| | 1 | | | 2 | | | 3 | | | 4 | | | |
| Distance from Hives (m) | A | B | Mean % | A | B | Mean % | A | B | Mean % | A | B | Mean % | MEAN %** |
| 3 | 0 | 0 | 0 | 0 | 1 | 2.5 | 0 | 1 | 2.5 | 1 | 1 | 5 | **2.5** |
| 40 | 0 | 0 | 0 | 0 | 0 | 0 | 0 | 2 | 7.5 | 1 | 0 | 2.5 | **2.5** |
| 80 | 1 | 0 | 2.5 | 2 | 0 | 7.5 | 0 | 0 | 0 | 0 | 0 | 0 | **2.5** |
| 120 | 1 | 0 | 2.5 | 2 | 0 | 7.5 | 0 | 1 | 2.5 | 1 | 0 | 2.5 | **3.75** |
| 160 | 0 | 0 | 0 | 1 | 0 | 2.5 | 0 | 0 | 0 | 0 | 2 | 7.5 | **2.5** |

RESULTS AND DISCUSSION—13 DAYS AFTER PLATING: Table 10 below shows results for assessments at 15 days after plating. This table shows an estimation for the mean percent of florets with *Clonostachys rosea*.

TABLE 10

| | Head number | | | | | | | | | | | | |
|---|---|---|---|---|---|---|---|---|---|---|---|---|---|
| | 1 | | | 2 | | | 3 | | | 4 | | | |
| Distance from Hives (m) | A | B | Mean % | A | B | Mean % | A | B | Mean % | A | B | Mean % | MEAN %** |
| 3 | 1 | 0 | 2.5 | 0 | 1 | 2.5 | 0 | 1 | 2.5 | 1 | 1 | 5 | **3.1** |
| 40 | 1 | 0 | 2.5 | 2 | 2 | 15.0 | 0 | 3 | 12.5 | 0 | 0 | 0 | **15.0** |
| 80 | 3 | 1 | 15.0 | 4 | 2 | 15.0 | 0 | 0 | 0 | 0 | 0 | 0 | **7.5** |
| 120 | 3 | 2 | 20.0 | 3 | 0 | 12.5 | 1 | 1 | 5.0 | 1 | 2 | 10.0 | **11.9** |
| 160 | 0 | 0 | 0 | 2 | 0 | 5.0 | 1 | 0 | 2.5 | 0 | 2 | 7.5 | **3.75** |

For both field 2 and field 3, the heads were kept in the patch bags used for sampling (bags open) after the florets had been removed. When examined at 9 days, some sporulation of *Clonostachys rosea* was found on various parts of some heads, including in some instances the central portion with no seeds. Sporulation was heaviest (as expected given the load of powder applied), but irregular, on the hand-inoculated heads. Certain other fungi (*Cladosporium*) were sporulating heavily; these may have extraordinary inoculums loads so get a "head start". An immature seed coincidentally plated with a colonized flower was absolutely covered with sporulation.

Example 4

Assessment of Seeds from Sunflowers Treated with Bumble Bee-Vectored *Clonostachys Rosea* Plus *Bacillus Thuringiensis* and Untreated Control Sunflowers Seed samples from field 1, described in example 3, and from untreated sunflowers were obtained. Sub-samples of each group of the seeds were plated on an agar medium to test for: Ability of the seeds to germinate properly; Presence/absence of *Clonostachys rosea*; Presence of other fungi on the seeds, including disease-causing pathogens.

Fifteen subsamples each of 40-50 seeds of each group (i.e. field #1 and control field) were plated onto PCA medium in Petri dishes. The medium contained Paraquat to accelerate tissue senescence and recovery of *Clonostachys rosea*, chloramphenicol (an antibacterial antibiotic), but no microbial nutrients. Most subsamples contained a few blackish fragments of other parts of sunflower heads. The dishes were incubated in plastic boxes in and examined at intervals over 2 weeks using a dissecting microscope and compound microscope as needed.

Results:

Seed Germination: Control sunflowers—70.7%; Sunflowers from Field 1-89.7%.

Thus germination of seeds from the bee vectored treatment described above was about 27% higher than in the untreated controls.

The mean values include only those seeds that produced good healthy radicals. Those that produced no radicals or radicals that aborted immediately (e.g. were brown when emerging) were rated as non-germinated.

Actual Values for Non-Germination:

Control: 10/48, 16/56, 10/42, 20/49, 14/38, 10/40, 14/44, 4/28, 16/40, 12/36, 8/30, 6/28, 12/39, 13/45, 12/41. 177/604=29.3%

Bee-vectored: 4/32, 8/46, 10/54, 4/51, 2/28, 4/48, 2/41, 4/62, 6/44, 4/49, 9/50, 2/36, 2/35, 3/35, 4/49. 68/660=10.3%

Recovery of *Clonostachys Rosea: Clonostachys rosea* did not sporulate on any of the sunflower seeds within the 14-day period of observations. *Clonostachys rosea* did sporulate on a few of the tissue fragments that are assumed to be from the sunflower heads, but only in the bee vectored materials.

At this point it seems that *Clonostachys* does not establish in sunflower seeds, or if it does, does not readily grow out from them.

Other Fungi: It was clear that moulds were much more abundant on seeds from the control field than in seeds from field 1. In the control seeds: *Fusarium* spp—very common; *Penicillium* spp—common; *Botrytis cinerea*—moderately common; other moulds with no spores 9 just mycelium, so were not identified). In the seeds from field 1: *Fusarium* spp, *Penicillium* spp, and some *Rhizopus*, but all much less frequent than in controls. No *Botrytis* found.

In both samples, some seeds appeared to abort on account of one or more of these fungi.

*Cladosporium* and *Alternaria* were common on the seed testas ("husks" or "shells") of both seed lots but did not appear to be causing any problems.

The findings indicate that the treatment disclosed herein enhanced germination of the sunflower seeds by 27% and greatly reduced the level of fungi (moulds) present.

The invention claimed is:

1. A formulation for treatment of plants, the formulation comprising:

a) a particulate calcium silicate;

b) a plant treatment agent combined with the particulate calcium silicate;

c) between about 0.5 wt % and 5 wt % moisture absorption agent;

d) between about 50 wt % and 75 wt % diluent; and e) between about 0.75 wt % and 5.0 wt % anti-caking agent;

wherein the plant treatment agent comprises at least one of *clonostachys rosea* and *beauveria bassiana*, the plant treatment agent is bonded to at least some of the calcium silicate to form stabilized plant treatment particles, and at least some of the calcium silicate is free calcium silicate.

2. The formulation of claim 1, wherein the formulation comprises between about 10 wt % and 25 wt % free calcium silicate and between about 5 wt % and 15 wt % stabilized plant treatment particles.

3. The formulation of claim 1, wherein the plant treatment agent comprises a fungal spore.

4. The formulation of claim 1, wherein:

a) the plant treatment agent comprises a fungal spore;

b) the plant treatment agent has a density of between about $1\times10^9$ and $4\times10^9$ spores per gram of calcium silicate to which it is bonded.

5. The formulation of claim 1, wherein the moisture absorption agent comprises silica gel.

6. The formulation of claim 1, further comprising an attracting agent.

7. The formulation of claim 6, wherein the attracting agent has a net positive electrostatic charge.

8. The formulation of claim 6, wherein the attracting agent comprises a mixture of minerals.

9. The formulation of claim 1, wherein the diluent comprises a flour.

10. The formulation of claim 1, wherein the anti-caking agent comprises magnesium oxide.

11. A method of plant treatment comprising at least one of (i) using the formulation of claim 1 to treat at least one of *sclerotinia sclerotiorum, botrytis cinerea*, and *Monilinia vaccinii-corymbosi* in a plant (ii) using the formulation of claim 1 to treat a disease in at least one of canola plants and sunflower plants, and (iii) using the formulation of claim 1 to treat a crop to increase the germination rate in the crop.

12. A method of bee vectoring comprising: applying the formulation of claim 1 to a bee as a bee vectoring agent.

13. The formulation of claim 6, wherein the formulation comprises between about 5 wt % and about 20 wt % attracting agent.

14. The formulation of claim 6, wherein:

the particulate calcium silicate comprises particles having a sieve designation of between about 45 microns and about 75 microns;

the moisture absorption agent comprises particles having a sieve designation of between about 700 microns and 4000 microns;

the attracting agent has a sieve designation of between about 35 microns and about 75 microns;

the diluent has a sieve designation of between about 75 microns and about 250 microns; and the anti-caking agent has a sieve designation of between about 75 microns and about 150 microns.

* * * * *